US011000188B2

(12) United States Patent
Farahbakhshian et al.

(10) Patent No.: US 11,000,188 B2
(45) Date of Patent: May 11, 2021

(54) SMART BODY ANALYZER WITH 3D BODY SCANNER AND OTHER VITAL PARAMETER SENSORS

(71) Applicant: Naked Labs Austria GMBH, Vienna (AT)

(72) Inventors: Farhad Farahbakhshian, Redwood City, CA (US); Peter Kreuzgruber, Vienna (AT)

(73) Assignee: NAKED LAB AUSTRIA GMBH, Vienna (AT)

( * ) Notice: Subject to any disclaimer, the term of this patent is extended or adjusted under 35 U.S.C. 154(b) by 203 days.

(21) Appl. No.: 16/316,792

(22) PCT Filed: Jul. 13, 2017

(86) PCT No.: PCT/EP2017/067664
§ 371 (c)(1),
(2) Date: Jan. 10, 2019

(87) PCT Pub. No.: WO2018/011330
PCT Pub. Date: Jan. 18, 2018

(65) Prior Publication Data
US 2020/0178807 A1    Jun. 11, 2020

(30) Foreign Application Priority Data
Jul. 13, 2016    (DE) ............... 10 2016 112 894.5

(51) Int. Cl.
*A61B 5/00*    (2006.01)
*A61B 5/01*    (2006.01)
(Continued)

(52) U.S. Cl.
CPC ............ *A61B 5/0064* (2013.01); *A61B 5/015* (2013.01); *A61B 5/02116* (2013.01);
(Continued)

(58) Field of Classification Search
None
See application file for complete search history.

(56) References Cited

U.S. PATENT DOCUMENTS

2004/0030383 A1\* 2/2004 Havey ................ A61N 1/36046
623/4.1
2008/0245972 A1\* 10/2008 Drapeau .............. A61B 5/0064
250/475.2

(Continued)

FOREIGN PATENT DOCUMENTS

CN    103606187    2/2014
EP    2258265    12/2010

OTHER PUBLICATIONS

International Search Report, PCT/EP2017/067664, dated Sep. 28, 2017, 3 Pages.
(Continued)

*Primary Examiner* — Paula J Stice
(74) *Attorney, Agent, or Firm* — Dority & Manning, P.A.

(57) ABSTRACT

A smart body analyzer apparatus includes a rotatable plate for supporting and turning a body, a control unit for rotating the rotatable plate, and at least one group of touch-less sensors for scanning the body. Examples of touch-less sensors include a far infrared temperature sensor and a depth sensor. The depth sensor can employ a time-of-flight imaging method, a stereoscopic imaging method, a microwave imaging method and/or a laser ranging method based on trigonometric principles.

16 Claims, 1 Drawing Sheet

(51) Int. Cl.
*A61B 5/021* (2006.01)
*A61B 5/0507* (2021.01)
*A61B 5/107* (2006.01)
*A61B 5/16* (2006.01)

(52) U.S. Cl.
CPC .......... *A61B 5/0507* (2013.01); *A61B 5/1072* (2013.01); *A61B 5/1077* (2013.01); *A61B 5/16* (2013.01)

(56) References Cited

U.S. PATENT DOCUMENTS

| | | |
|---|---|---|
| 2010/0123078 A1 | 5/2010 | Guinta |
| 2010/0191541 A1 | 7/2010 | Prokoski |
| 2011/0297828 A1* | 12/2011 | Weisbach ........... H04N 5/35581 |
| | | 250/330 |
| 2012/0326959 A1 | 12/2012 | Murthi et al. |
| 2013/0021373 A1* | 1/2013 | Vaught .................... G06F 3/013 |
| | | 345/633 |
| 2013/0123015 A1 | 5/2013 | Jung et al. |
| 2014/0184496 A1* | 7/2014 | Gribetz ................ G02B 27/017 |
| | | 345/156 |
| 2014/0340479 A1 | 11/2014 | Moore et al. |
| 2016/0144278 A1* | 5/2016 | el Kaliouby ........... G16H 50/30 |
| | | 463/36 |
| 2017/0319148 A1* | 11/2017 | Shahin ................... A61B 5/015 |
| 2018/0137640 A1 | 5/2018 | Farahbakhshian et al. |

OTHER PUBLICATIONS

Written Opinion of International Searching Authority, PCT/EP2017/067664, dated Oct. 9, 2017, 15 Pages.
International Preliminary Report on Patentability, PCT/EP2017/067644, dated Jan. 24, 2019, 2 pages.
Written Opinion of the International Searching Authority, PCT/EP2017/067644, dated Jan. 24, 2019, 9 pages.

* cited by examiner

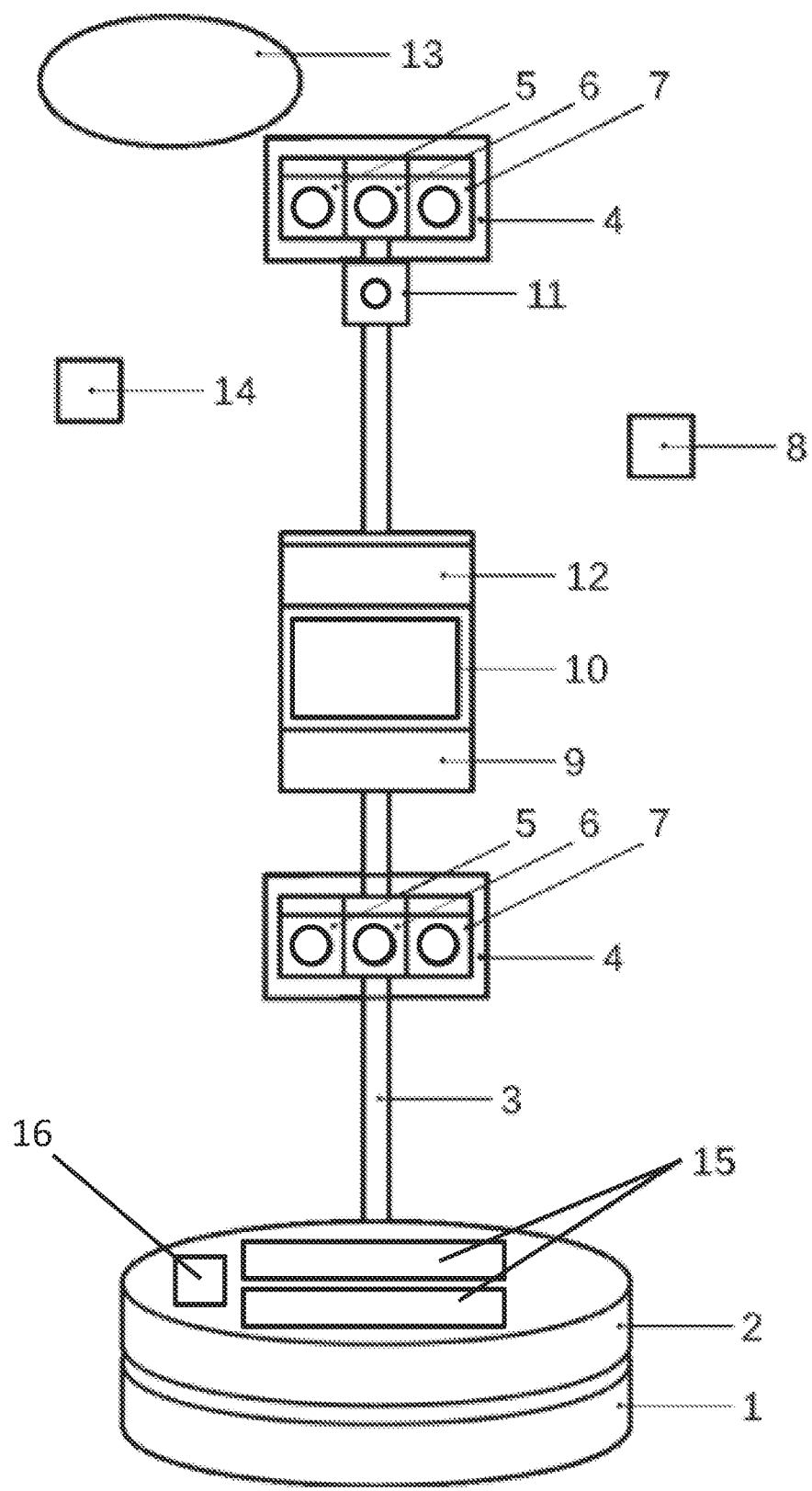

SMART BODY ANALYZER WITH 3D BODY SCANNER AND OTHER VITAL PARAMETER SENSORS

CROSS-REFERENCE TO RELATED APPLICATIONS

The present application is related by subject matter to the following concurrently filed PCT applications (all of which designate the US):

a. International Application No.: PCT/EP2017/067668; entitled "Determination of Body Fat Content by Body-Volume-Distribution and Body-Impedance-Measurement".

b. International Application No.: PCT/EP2017/067669; entitled "Optical Marker to Adjust the Turntable of a 3D Body Scanner".

c. International Application No.: PCT/EP2017/067761; entitled "Efficient Volumetric Reconstruction with Depth Sensors".

d. International Application No.: PCT/2017/067672; entitled "Skeleton Estimation from Body Mesh".

e. International Application No.: PCT/2017/067667; entitled "Method for Creating a 3D-Model and 3D-Body-Scanner".

f. International Application No.: PCT/2017/067664; entitled "Smart Body Analyzer with 3D Body Scanner and Vital Parameter Sensors", which claims priority to German Application No.: DE10 2016 112 894.5.

g. International Application No.: PCT/EP2017/067665; entitled "Motor Driven Turntable with Foldable Sensor Mast," which claims priority to German Application No.: DE 10 2016 112 893.7.

h. International Application No.: PCT/EP2017/067671; entitled "Alignment of Scan Parts on a Turntable," which claims priority to German Application No.: DE 10 2016 112 890.2.

The above cited PCT international applications are hereby incorporated herein in their entireties by this reference for all purposes. Any combination of the features and aspects of the subject matter described in at least one of the incorporated applications may be combined with embodiments of the present application to yield still further embodiments of the present invention.

FIELD OF THE INVENTION

The invention relates to a smart body analyzer apparatus comprising a control unit, a rotating plate for turning a body controlled by the control unit and at least one group of touch-less sensors for scanning the body, which comprises a far infrared temperature sensor and a depth sensor working with a time-of-flight imaging method, a stereoscopic imaging method, a microwave imaging method and/or a laser ranging method based on trigonometric principles.

The invention relates generally to a smart body analyzer that can measure mechanical-, health- and mood parameters of the user—e.g. body volume, body composition, body dimensions, body mass, heart rate, skin temperature, blood pressure, blood oxygen content, musculature tension, skin humidity—by the means of a three dimensional body scan comprised by the measurement of further parameters with other sensors. The obtained information is analyzed and the parameters of merit may be extracted. The results may be stored in a data-base, that may be accessible e.g. via smartphone, tablet, browser, notebook and/or desktop computer.

BACKGROUND OF THE INVENTION

The state of art smart body analyzers fall into 3 categories:
1. Single value measurement instrumentation with no intelligence like simple body scales, body size measurement sticks, fever thermometers and so on.
2. Measurement instrumentation with a rough indirect parameter estimation like scales processing the body mass index from measured weight and entered body height, age and gender. Another example is body fat content from analysis from weight and an impedance measurement.
3. Measurement instrumentation of two parameters like body mass and height, weight and body impedance measurement as a rough indication of body fat content, blood pressure and heart rate or blood oxygen saturation and heart rate.

Some of such measurement systems with connectivity may memorize and track the users' parameters and display them either through a browser or an app on a smart phone.

The state of the art systems have the following shortcomings:

Prior art does not measure the volume of the body.

Prior art does not measure the physical constitution of the body like arm and leg length.

Prior art makes calculation of indirect derived parameters (e.g. body mass index) from one measured and other entered values by calculating with equations derived from the average of the population. This leads to extremely inaccurate results.

Prior art does not measure more than two body parameters.

Prior art is not intelligent enough to make any assessments or diagnostics about the user with the limited measurements it has made.

Prior art does not measure any other valuable health parameters together with mass like blood pressure, heart rate, blood oxygen content, lung volume or the temperature measurement of the user in the course of the body measurement.

Prior art does not derive mood of the user.

Prior art does not derive stress level or tiredness of the user.

Prior art does not recommend measures to improve health, fitness, or reduce stress.

According to the state of the art, physical, vital and emotional body parameters are measured in a fragmented way by different equipment like length measurement tapes, scales, temperature meters and blood pressure measurement equipment. Some of this instrumentation may be linked to a computer to store data. Others are not. Especially obtaining the physical data of the body like length, volume and constitution is currently the domain of heavy medical equipment and not available in a low cost way usable for private applications. Also the combination of this data to obtain more complicated body parameters is not properly solved yet.

Brief Objects and Summary of the Invention

The object of the present invention is to provide a Smart body analyzer apparatus, which eliminates theses disadvantages.

The aforementioned object is achieved by means of a smart body analyzer apparatus exhibiting the features disclosed in the description that follows.

Proposed is a smart body analyzer apparatus comprising a control unit, a rotating plate for turning a body controlled by the control unit, and at least one group of touch-less sensors for scanning the body. The at least one group of touch-less sensors comprises a far infrared temperature sensor and a depth sensor. The depth sensor is designed in such a way that it works with a time-of-flight imaging method, a stereoscopic imaging method, a microwave imaging method and/or a laser ranging method based on trigonometric principles.

It is advantageous if the depth sensor is a stereoscopic depth sensor and/or comprises two cameras, which are spaced apart from one another.

In an advantageous further aspect, the two cameras are spaced apart from one another with respect to the rotating plate, in a vertical direction.

It is advantageous if the group of touch-less sensors comprises at least one high resolution, color camera.

It is advantageous if the control unit is designed in such a way that it scans the face of the user with the color camera in conjunction with the depth sensor and recognizes the mood of the user.

It is advantageous if the color camera is at the same time a camera of the depth sensor.

In an advantageous further aspect, the apparatus comprises a second group of touch-less sensors for scanning the body, in particular according to the previous specification.

It is advantageous if the first and second group of touch-less sensors are spaced apart from one another with respect to the rotating plate in vertical direction.

It is advantageous if the first group of touch-less sensors comprises a bottom detection zone and the second group of touch-less sensors comprises a top detection zone, in particular with a common overlapping area.

In an advantageous further aspect, the apparatus comprises a scale for measuring the weight of the body, which is in particular integrated into the rotating plate.

It is advantageous if the apparatus comprises at least one auxiliary body function sensor, in particular a blood pressure sensor, heart rate, a blood oxygen saturation sensor, a body conductivity sensor and/or a breathing air flow sensor.

In an advantageous further aspect, the apparatus comprises a wireless communication inter-face, in particular WiFi, Bluetooth or ZigBee, for connecting the control unit wireless with the auxiliary sensor, the rotating plate, the scale, a cloud, a local cloud data base, a smart-phone, a tablet, a laptop and/or a PC.

It is advantageous if the apparatus comprises a mast, which is in particular separated from the rotating plate and/or which carries the control unit, the at least one group of touch-less sensors and/or the wireless communication interface.

It is advantageous if the control unit is designed in such a way that it manages the operation of the rotary plate, the scale, the at least one group of touch-less sensors and/or the at least one auxiliary body function sensor.

It is advantageous if the smart body analyzer apparatus comprises at least one of the following features:

It is advantageous if the smart body analyzer apparatus is designed in such a way that it can measure in a convenient way body mass, body volume in the form of a 3D scan, skin temperature, heart rate, body composition and/or facial mood recognition of the user.

It is advantageous if the apparatus employs a depth sensor in conjunction with a color camera to scan the user's body in order to create an accurate 3D rendering of the body, which can be sent directly to the user via wireless or stored on the cloud. The accurate 3D scan from the apparatus allows the calculation of accurate body composition and tracking body dimensions.

It is advantageous if the depth sensor and color camera are also used to scan the face of the user to recognize the mood, measure heart rate and measure body temperature.

It is advantageous if the temperature and heart rate measurement of the user's body are made with the use of the color camera in conjunction with the depth sensor.

It is advantageous if facial mood recognition is done via the use of color camera in conjunction with the depth sensor.

It is advantageous if the apparatus will use the combination of facial mood recognition, body temp and/or heart rate to diagnose certain medical conditions.

BRIEF DESCRIPTION OF THE DRAWING

Additional advantages of the invention are described in the following exemplary embodiments. The drawings show in:

FIG. 1 realization example of the smart body analyzer in particular with 3D body scanner and other vital parameter sensors.

DETAILED DESCRIPTION OF EXEMPLARY EMBODIMENTS OF THE INVENTION

The invented apparatus shown in FIG. 1 is composed in an advantageous way by a rotating plate 1 driven by a motor 16, a scale 2 and a mast 3 carrying at least one, typically but not limited to two groups of touch-less sensors 4, a control unit 9, a manual and optical user interface 10, an acoustic user interface 11 and a communication interface 12.

The rotating plate 1 turns around and the user carried on the plate 1 and is controlled by the control unit 9 to ensure that the whole body is visible by the groups of touch-less sensors 4. The control unit is configured with the ability to stop the rotating plate 1 at any angle.

The groups of touch-less sensors 4 contain a depth sensor 5, a high-resolution color camera 6 and a far infrared temperature sensor 7. Multiple groups of touch-less sensors 4 are used at different heights above the plate 1 to capture the full body surface over the height of the user.

The other sensors include auxiliary body function sensors 8, which may be, but not limited to, a blood pressure sensor, a blood oxygen saturation sensor, a body conductivity sensor connected to the recommended foot positions 15 on the scale 2, and a breathing air flow sensor, each of which being connected e.g. by a wireless link to the control unit 9.

The communications interface 12 connects, e.g. in a wireless way, the control unit 9 with the scale 2, the rotating plate 1 and/or the auxiliary sensors by for example, but not limited to Bluetooth, Bluetooth low energy, ZigBee or any proprietary RF connection. Furthermore the communications interface 12 connects the invention, e.g. in a wireless way, with e.g. a cloud or local cloud data base or with a Smart-phone/Tablet/laptop/PC 14 for on-line or off-line visualization and presentation of the results.

The control unit 9 manages under control of the manual and optical user interface 10 and/or the acoustic user interface 11, the operation of the rotary plate 1, the scale 2, the group of touch-less sensors 4 and/or the auxiliary body function sensors 8.

The control unit 9 also collects measurement results of the scale 2, the raw 3D depth scan data of the multiple depth sensors 4, the color image data of the multiple high resolution color cameras 6 and/or the body temperature data of the multiple far infrared temperature sensors 7 and/or the other vital measurement values obtained from the auxiliary body function sensors 8 like but not limited to, blood pressure, blood oxygen saturation, body conductivity and/or breathing air flow of the auxiliary body function sensors 8.

Because each group of touch-less sensors 4 may see only a part of the user's body, each group of touch-less sensors 4 may deliver only a part of the entire body scan image. The control unit 9 calculates from the raw data delivered by the 3D depth sensors 5 scans of a part of the user's body, a full 3D depth scan model of the user's body by combining and eliminating of shadowing effects.

From partial images of the body taken by each of the color cameras 6, the control unit 9 calculates a 3D color image of the user's entire body. Also here shadowing effects are eliminated by combining of the partial images obtained from different positions by the color cameras 6. From partial images of the body taken by each of the far infrared temperature sensors 7, the control unit 9 calculates in the same way a 3D thermal image of the user's entire body.

From the body mass measured by the scale 2 and the 3D full body scan image, the control unit 9 calculates basic body parameters as are but not limited to: body height, body mass, body volume, body composition and/or clothing retail parameters.

From measurement of the short-term changes of the body during the scanning process like but not limited to: chest motion, eye closing and/or musculature tension and/or tremor, further significant body parameters like but not limited to: breathing rate, breathing volume, heart rate, tiredness and/or temporary physical overstress can be derived.

From the parameters above and measurement values from the auxiliary body function sensors 8 as are for example but not limited to: heart rate, blood pressure, blood oxygen content, body conductivity and/or breathing air flow, together with given age and gender of the user, the control unit 9 is configured to calculate indirect fitness-, stress-, health-, as are but not limited to: body mass index, body fat content, muscle improvement/decline with respect to different stimuli such as diet and/or exercise posture analysis along with improvement techniques, body metabolism, heat maps of muscle density and/or body balance.

The analysis of mid-term and long-term changes of the body parameters are stored either in the control unit 9, in the private or public cloud data base 13 and/or in the smart-phone/tablet/laptop/PC 14. The fitness-, stress- and/or health-behave of the user can be monitored and controlled. By comparing the skin images from the high-resolution color camera 6 with the history, the control unit 9 can generate a skin-cancer pre-warning.

By analysis of the skin temperature images from the far infrared temperature sensor 7, a fever or sub-cutaneous inflammation warning can be given by the control unit 9.

The display of the manual and optical user interface 10 will show information such as 3D body scan, mass, body composition and/or other results or warnings by the control unit 9.

The acoustic user interface 11 will accept spoken commands by the user like but not limited to "start scan" and/or "stop scan" and/or guide the user acoustically through the scan process. Background music and/or commercials provided by the acoustic user interface 11 can provide distraction that will seem to shorten the time of the scanning process for the user.

The depth sensors 5 may be realized by any 3D imaging method like but not limited to stereoscopic cameras, time of flight cameras, microwave imaging, ultrasonic imaging and/or laser ranging on trigonometric principles.

Using dynamic movement information obtained from such as the 3D depth image and color camera and the group of touch-less sensors, the mood of the user can be approximated by the control unit 9 using the facial expression, heart-rate, temperature and/or complexion of the user.

By analyzing the shape and changes in the 3D scans of the body, which are obtained by the touch-less sensors 4, and/or the computation of body composition, heat maps of muscle density and/or fat distribution can be obtained by the control unit 9.

An apparatus is provided that combines the measurement of the physical dimensions (size volume) of the user's body obtained by a three dimensional scan of the user's body turning around on a rotating plate 1 with one or more depth sensors 5.

A 3D color image of the body is obtained by one or more high resolution color cameras 6. A 3D thermal image of the body is obtained by one or more infrared sensors 7.

The weight of the body is measured by a scale 2 along with other vital body functions that are measured by one or more different auxiliary body function sensors 8.

The apparatus calculates in the control unit 9 from the signals of the sensor/s, a number of body parameters, e.g. body-size, body-weight, body-constitution, cloth sizes, fitness parameters, mood-level, stress-level and/or health-level, and the apparatus may display this information on the display of a manual and optical user interface 10.

The apparatus may send this information for storing via a communication interface 12 e.g. to a private or public cloud data base 13, or for presentation or post processing e.g. to a smart-phone/tablet/laptop/PC 14.

The apparatus may create a 3D scan image from a human body by using more than one of the depth sensors 5 which contributes partial images of the body that are combined to a particularly complete 3D image of the body in way that avoid non modeled parts of the body that arise due to shadowing effects of the body's contours.

The apparatus may create a 3D color scan image from a human body by using preferably more than one of the high resolution color cameras 6 which contribute partial images of the body that are combined to a particularly complete 3D image of the body in way that avoids non modeled parts of the body that arise due to shadowing effects of the body's contours.

The apparatus may create a 3D color scan image from a human body by using preferably more than one far infrared temperature sensor 7 which contribute partial images of the body that are combined to a particularly complete 3D image of the body in way that avoids non modeled parts of the body that arise due to shadowing effects of the body's contours.

As schematically shown in FIG. 1, the apparatus may include a rotating plate 1, a scale 2 and/or a mast 3 carrying at least one, typically but not limited to two groups of touch-less sensors 4, a control unit 9, a manual and/or optical user interface 10, an acoustic user interface 11 and/or a communication interface 12.

The depth sensors 4 may be configured to employ any 3D imaging method like but not limited to stereo imaging, time-of-flight based depth cameras, microwave imaging, ultrasonic imaging and/or laser ranging based on trigonometric principles.

The apparatus may be configured to calculate from the 3D full body scan image, the basic physical body parameters as are but not limited to body height, body volume, and/or body composition.

The apparatus may precisely calculate clothing retail size numbers from the basic physical body parameters.

Using the measurement values from the scale 2 and/or the auxiliary body function sensors 8 and/or the age and/or gender of the user, the apparatus is configured to automatically calculate fitness-, stress-, and/or health-, parameters of the user.

The apparatus may give the user a friendly warning if the vital body parameters like for example, but not limited to, weight related to body composition, tiredness, body temperature, heart rate, breathing rate, breathing volume, blood pressure, when any of these might exceed the commonly accepted health limits.

The apparatus may compare the actual measurement values, vital-fitness-, stress- and/or health-parameters of the user with their history stored in for example but not limited to the control unit 9, the private and/or public cloud data base 13 and/or a smart-phone/tablet/laptop/PC 14 wherein the control unit 9 is configured to track and/or display their changes and give the user a friendly warning at unhealthy deviations.

The apparatus may compare the high-resolution color images from the past with the actual ones to give e.g. a skin cancer pre-warning.

The apparatus may use a wireless connection for example, but not limited to Bluetooth, Bluetooth low energy, ZigBee and/or any other public or proprietary RF connection between the control unit 9 and the auxiliary body function sensors 8 to avoid cabling problems when rotating the user's body by the turn table 1.

The auxiliary body function sensors 8 may be third party vital body parameter sensors, which are so called "wearables".

The acoustic user interface 11 allows in an advantageous way, control of a standstill body, which may be a precondition for a successful scan, and even if the manual and optical user interface 10 is out of reach- and thus beyond the visibility distance of the user.

The at least one depth sensor 5 can be also configured to include high-resolution, color cameras 6. In this case the color camera 6 is one of the two cameras of the depth sensor 5.

The at least one depth sensor 5 can be also configured to include one or more high-resolution, color camera/s 6 generating a stereo effect by the rotation of the users by the rotation plate 1.

The apparatus may be simplified so that instead of using the depth sensors 5, only one or more high-resolution color cameras 6 can be used to record pictures of the body in one or more angles of the rotating plate 1 and/or to calculate the 3D body parameters from the circumference of the body of the user obtained from the photos.

The invention is not limited to the embodiments shown or described. Rather, any and all combinations of the individual features described, as shown in the figures or described in the description, and to the extent that a corresponding combination appears possible and sensible, are subject matters of the invention.

To measure size, weight, constitution, fitness, mood-, stress- and/or health level, of a person today, needs a number of separate technical instrumentation and/or analysis methods. The invention provides a compact apparatus and method to analyze a human body by the means of a scale, a 3D full body scanner on geometrical depth-, color imaging and/or body temperature imaging level combined with other vital body parameter sensors. From this, measurements of body-size, -weight, -constitution, cloth sizes, fitness parameters, mood-, stress- and/or health-level are automatically calculated and may be provided on various user interfaces. By comparing this data with images from the past, the development of the body, its fitness and/or health can be tracked.

LIST OF REFERENCE CHARACTERS

Rotating plate
Scale
Mast
Group of touch-less sensors
Depth sensor
Color camera
Far infrared temperature sensor
Auxiliary body function sensors
Control unit
Manual and optical user interface
Acoustic user interface
Communication interface
Private or public cloud data base
Smart-phone/Tablet/laptop/PC
Recommended foot positions

The invention claimed is:

1. An apparatus for analyzing a body of a person, the apparatus comprising:
a plate that is rotatable and configured for carrying the body;
a motor connected to the plate and configured for driving rotation of the plate;
a control unit connected to the motor for controlling operation of the motor;
a far infrared temperature sensor connected to the control unit and aimed to sense temperatures of the body carried by the plate; and
a depth sensor connected to the control unit and aimed to sense the body carried by the plate, the depth sensor including a color camera;
wherein the control unit is configured to employ the color camera to take partial images of the body and create an accurate 3D rendering of the bod from the partial images of the body taken by the color camera; and
wherein the control unit is configured to employ the far infrared temperature sensor to take partial images of the body and create an accurate 3D thermal image of the body from the partial images of the body taken by the far infrared temperature sensor.

2. Apparatus according to claim 1, wherein the depth sensor comprises a second camera, which is spaced apart from the color camera.

3. Apparatus according to claim 2, wherein the color camera and the second camera are spaced apart from one another in a vertical direction with respect to the plate.

4. Apparatus according to claim 3, wherein one of the cameras is a high resolution, color camera.

5. Apparatus according to claim 1, further comprising a second group of touch-less sensors connected to the control unit and configured and disposed for scanning the body carried by the plate, wherein the far infrared temperature sensor and the depth sensor form a first group of touch-less sensors.

6. Apparatus according to claim 5, wherein the first group of touch-less sensors is spaced apart in a vertical direction with respect to the plate from the second group of touch-less sensors.

7. Apparatus according to claim 6, wherein the first group of touch-less sensors comprises a bottom detection zone and the second group of touch-less sensors comprises a top detection zone, wherein a common overlapping region is shared by the top detection zone and the bottom detection zone.

8. Apparatus according to claim 1, further comprising a scale connected to the control unit and configured for measuring the weight of the body carried by the plate, wherein the scale is integrated into the plate.

9. Apparatus according to claim 8, wherein the control unit is designed in such a way that it manages the operation of the plate, the scale and the sensors.

10. Apparatus according to claim 1, further comprising a body function sensor connected to the control unit and configured and disposed to measure a body function of the body carried by the plate.

11. Apparatus according to claim 10, further comprising a wireless communication interface connecting the control unit with the body function sensor and a cloud, a local cloud data base, a smart-phone, a tablet, a laptop and/or a PC.

12. Apparatus according to claim 11, further comprising a mast, which is separated from the plate and which carries the control unit, the sensors or the wireless communication interface.

13. Apparatus according to claim 1, wherein the depth sensor is configured to employ a time-of-flight imaging method to sense the depth of the body carried by the plate.

14. Apparatus according to claim 1, wherein the depth sensor is configured to employ a stereoscopic imaging method to sense the depth of the body carried by the plate.

15. Apparatus according to claim 1, wherein the depth sensor is configured to employ a microwave imaging method to sense the depth of the body carried by the plate.

16. Apparatus according to claim 1, wherein the depth sensor is configured to employ a laser ranging method based on trigonometric principles to sense the depth of the body carried by the plate.

* * * * *